(12) United States Patent
Schaede

(10) Patent No.: US 7,215,427 B2
(45) Date of Patent: May 8, 2007

(54) DEVICE FOR CONTROLLING MATERIAL

(75) Inventor: Johannes Georg Schaede, Würzburg (DE)

(73) Assignee: KBA-Giori S.A., Lausanne (CH)

( * ) Notice: Subject to any disclaimer, the term of this patent is extended or adjusted under 35 U.S.C. 154(b) by 73 days.

(21) Appl. No.: 10/499,507

(22) PCT Filed: Dec. 12, 2002

(86) PCT No.: PCT/DE02/04609

§ 371 (c)(1),
(2), (4) Date: Jul. 12, 2004

(87) PCT Pub. No.: WO03/052394

PCT Pub. Date: Jun. 26, 2003

(65) Prior Publication Data

US 2005/0052711 A1   Mar. 10, 2005

(30) Foreign Application Priority Data

Dec. 18, 2001  (DE) ................................ 101 62 340
Apr. 18, 2002  (DE) ................................ 102 17 403

(51) Int. Cl.
*G01N 21/84*  (2006.01)
*H04N 1/04*  (2006.01)

(52) U.S. Cl. ...................... 356/429; 358/490; 358/493
(58) Field of Classification Search ............... None
See application file for complete search history.

(56) References Cited

U.S. PATENT DOCUMENTS

| | | | | |
|---|---|---|---|---|
| 3,574,263 | A | * | 4/1971 | Del Elia ...................... 434/355 |
| 4,233,663 | A | * | 11/1980 | Sugawara et al. .......... 358/296 |
| 4,259,591 | A | | 3/1981 | Morris et al. |
| 4,407,197 | A | | 10/1983 | Jeschke |
| 5,548,408 | A | * | 8/1996 | Koren ......................... 358/300 |
| 6,081,352 | A | * | 6/2000 | Poulsen et al. ............. 358/493 |
| 6,307,972 | B1 | * | 10/2001 | Riley et al. ................. 358/3.06 |

FOREIGN PATENT DOCUMENTS

| | | |
|---|---|---|
| CH | 466 330 A | 6/1969 |
| DE | 433 19 65 A | 3/1995 |

* cited by examiner

*Primary Examiner*—Michael P. Stafira
(74) *Attorney, Agent, or Firm*—Clifford W. Browning; Krieg DeVault LLP

(57) ABSTRACT

The invention relates to a device for controlling material comprising a sensor device and a lighting device, whereby the material which is to be controlled is guided on a transparent drum.

14 Claims, 3 Drawing Sheets

DEVICE FOR CONTROLLING MATERIAL

Figure 1:
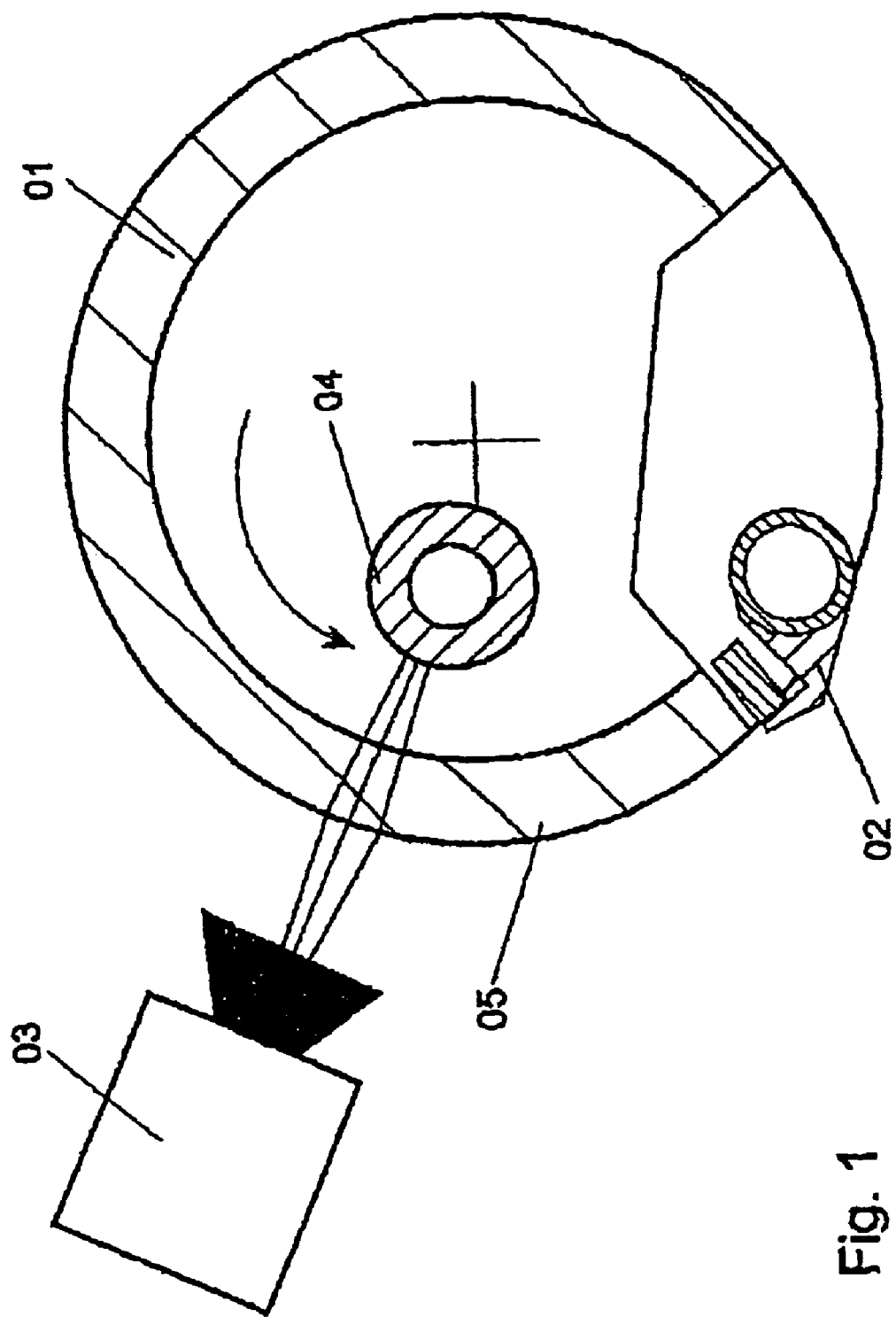

The invention relates to a device to control material according to the preamble of claim 1.

Such devices are known from DE 29 44 322 A1 and U.S. Pat. No. 3,028,502 A.

With the device described in U.S. Pat. No. 3,028,502 A, the material to be controlled is stretched on a transparent drum and can be passed by a sensor unit by means of a corresponding drum rotation. The sensor is installed inside the drum and can be moved via a mobile runner in the direction of the longitudinal axis of the drum. Outside the drum, a lighting unit, that can be moved synchronous to the movement of the sensor unit, is arranged opposite the sensor unit. Through operation of the lighting unit, the printed image printed on the material can be illuminated, whereby, due to the transparent properties of the drum, the sensor unit inside the drum receives an input signal that changes in accordance with the printed image.

With the device described in DE 29 44 322 A, light-optical sensors are arranged within a transparent hollow drum. Outside the drum, there are light sources arranged opposite the light sensors, or a light source arranged over the entire length of the drum. Through illumination of the printed material stretched on the drum, depending on the printed color density, differing light intensities are detected by the sensors.

WO 01 85 586 A1 discloses a device to transport sheet material, in particular securities. So that the light from a light source can pass from outside the drum, with illumination of the printed material, to a sensor unit within the drum, the non-transparent drum has suitably-arranged openings so that, as an overall result, the entire surface area cannot be controlled.

DE 43 31 965 A1 shows a device to inspect X-ray images whereby the light source lies within a transparent drum.

The aim of the invention is to provide a device to control material.

This task is solved through the features of claim 1.

One advantage of the invention in particular is that the sensor unit placed outside the transparent drum is exposed to far less temperature load. Due to the position of the sensor unit outside the drum, it is possible to easily provide adequate cooling of the sensor.

One exemplifying embodiment of the invention is shown in the drawings and will be described below in greater detail.

Figure 2:
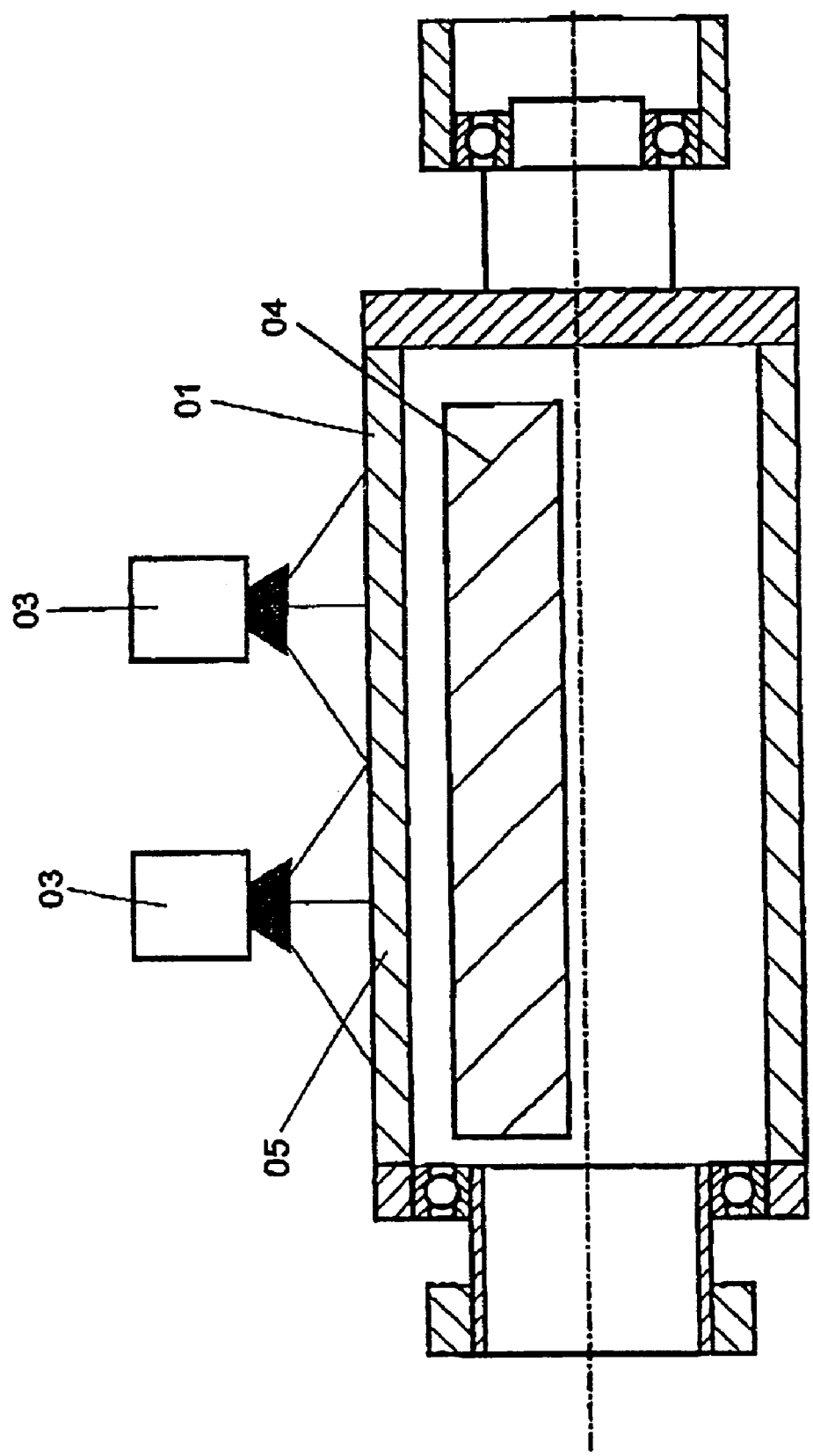
Figure 3:
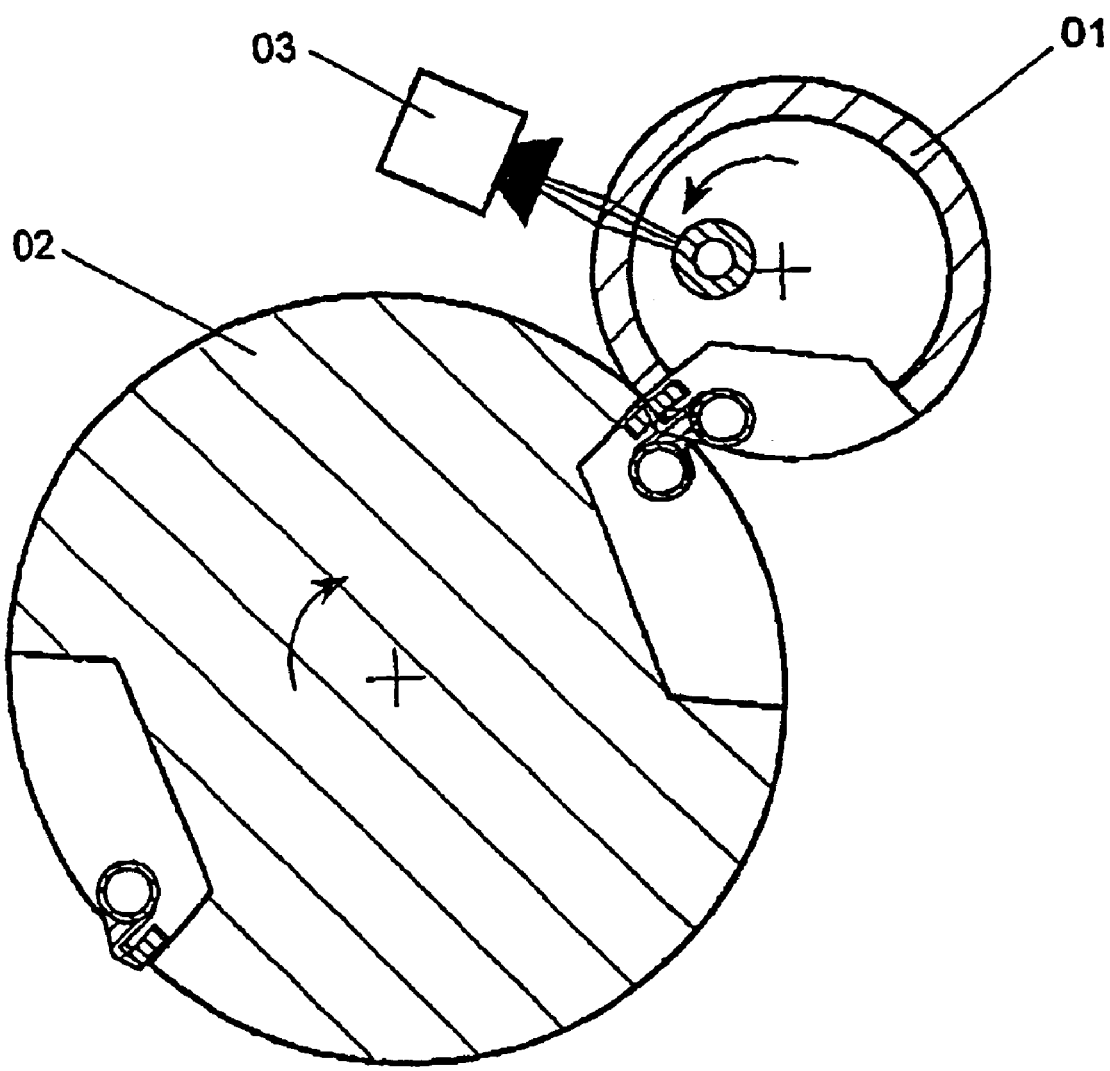
Figure 3:
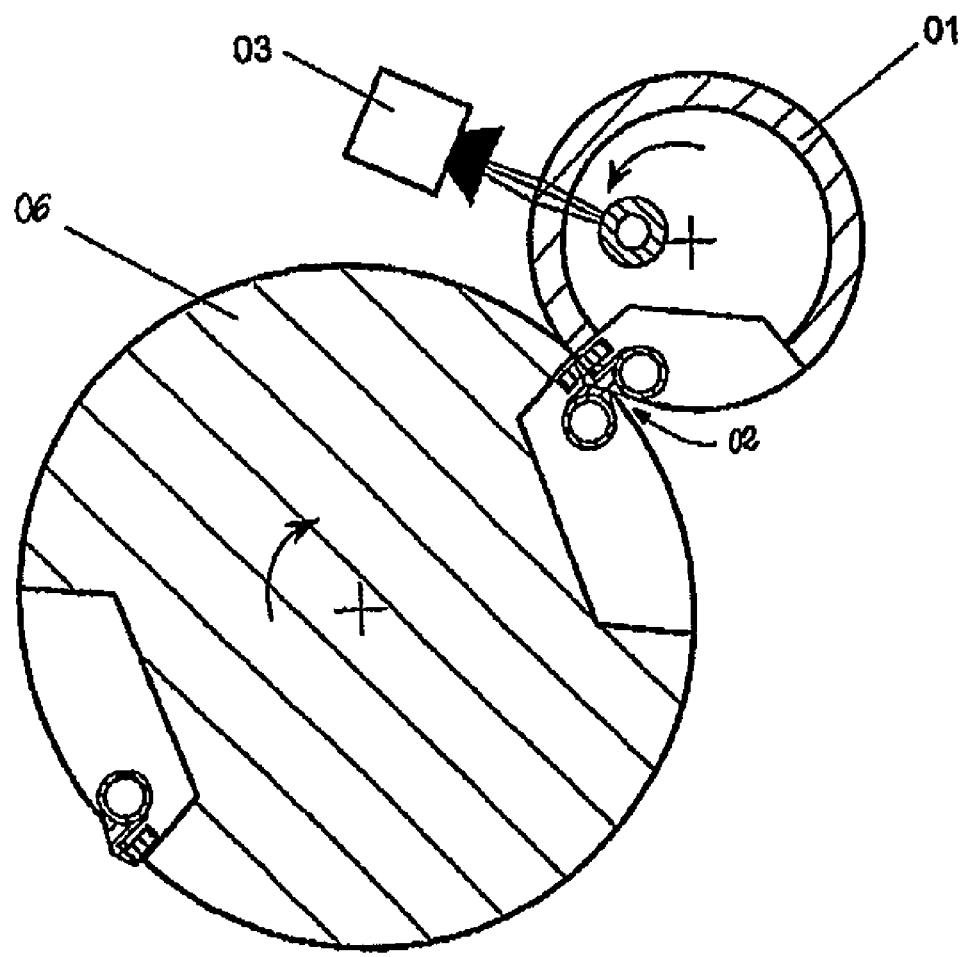

The following is shown:

FIG. 1 a device in cross-section;

FIG. 2 the device according to FIG. 1 in longitudinal section;

FIG. 3 the device according to FIG. 1 with the arrangement of a counter-pressure cylinder in a printing machine.

The device shown in FIG. 1 essentially consists of a transparent drum 01 with a retaining device 02, e.g. a gripper 02 and a sensor unit 03, e.g. a CCD camera 03, arranged outside the drum 01 and opposite a lighting unit 04 arranged inside the drum 01.

To control a material 05, especially a sheet printed with securities, the material 05 is fixed to the gripper 02 so that it can be moved along by rotational drive of the drum 01. Here the material 05 surrounds the drum 01 and nearly its entire surface lies on the transparent drum 01.

Through switching on the lighting device 04, the transparent drum 01 and the adjacent material 05 are illuminated and passed through by light beams, that then enter the lens of the sensor 03. Depending on the printed image on the material 05, the input signal detected by the sensor unit 03 changes such that, by means of a suitable evaluation unit, the printed image on the material 05 can be controlled through evaluation of the output signals from the sensor unit 03.

FIG. 2 shows the device with the drum 01 the sensor unit 03, the lighting unit 04 and the material to be controlled 05 in longitudinal section. It can be seen that the drum 01 is closed on the one front side and open on the other, so that adequate mechanical stability is ensured for the drum 01, and moreover the lighting unit 04 can readily be introduced within the drum 01 and fixed. Through the arrangement of the sensor unit 03 outside the drum 01, the sensors 03, shown in this example as two CCD cameras 09 arranged side by side, are easy to cool.

The lighting unit 04, constituted for example as a type of lighting tube 04, extends substantially over the entire length of the drum 01, so that the material 05 on the drum 01 can be illuminated in all areas. The lenses of the CCD cameras 03 are designed such that each covers half the length of the drum 01.

FIG. 3 schematically shows the device with the drum 01 and the sensor 03 arranged on a counter-pressure cylinder 06 in a securities-printing machine. By means of corresponding arrangement of the grippers 02 on the drum 01 and the counter-pressure cylinder 06, the securities printed in the printing machine can be continuously transferred from the counter-pressure cylinder 06 to the drum 01 and controlled there by the sensor 03.

REFERENCE LIST

01 Drum, transparent
02 Holding device, gripper
03 Sensor unit, CCD camera
04 Lighting unit, lighting tube
05 Material, to be controlled
06 Counter-pressure cylinder

The invention claimed is:

1. Device for controlling sheet material, with a sensor unit and a lighting unit, wherein the material to be controlled is led on a transparent drum, wherein the lighting unit is arranged on one side of the drum and the sensor unit on the other side of the drum, wherein the material has a printed image to be controlled, wherein the drum has a holding device for the sheet material to be controlled, and wherein this holding device comprises grippers which are an integral part of the drum for continually accepting the material and transferring it onto the drum.

2. Device according to claim 1, wherein the lighting unit is arranged within the periphery of the drum and the corresponding sensor unit is arranged outside the periphery of the drum.

3. Device according to claim 1, wherein the lighting unit and the corresponding sensor unit are arranged in a fixed manner.

4. Device according to claim 1, wherein the material is lying substantially over its entire surface upon the transparent drum.

5. Device according to claim 1, wherein the drum is provided as a rotating drum.

6. Device according to claim 1, wherein the drum is arranged in a printing machine.

7. Device according to claim 1, wherein the holding device accepts the material from a counter-pressure cylinder of a printing machine.

8. Device according to claim 1, wherein the sensor unit is a CCD camera.

9. Device according to claim 1, wherein the sensor unit controls securities printed on the material.

10. Device according to claim 1, wherein the sensor unit is arranged such that the material can be controlled without relative movement between material and sensor unit.

11. Device according to claim 1, wherein the lighting unit extends substantially over the entire length of the drum.

12. Device according to claim 1, wherein the sensor unit is cooled.

13. Device according to claim 1, wherein the drum is open at one front end and closed at the other.

14. Device according to claim 11, wherein the lighting unit comprises a lighting tube.

* * * * *

UNITED STATES PATENT AND TRADEMARK OFFICE
CERTIFICATE OF CORRECTION

PATENT NO.        : 7,215,427 B2
APPLICATION NO.  : 10/499507
DATED             : May 8, 2007
INVENTOR(S)       : Schaede It is certified that error appears in the above-identified patent and that said Letters Patent is hereby corrected as shown below:

On the Title page of the patent, under "(22) PCT Filed", please delete "Dec. 12, 2002" and insert in lieu thereof -- Dec. 17, 2002 --

Delete Drawing Sheet and substitute attached sheet. Corrected Fig. 3.

Signed and Sealed this

Tenth Day of July, 2007

JON W. DUDAS
*Director of the United States Patent and Trademark Office*